(12) United States Patent
Parkanyi et al.

(10) Patent No.: US 9,758,488 B2
(45) Date of Patent: Sep. 12, 2017

(54) METHOD FOR PREPARING PHENYLOXYMETHYL-NITRO-IMIDAZOLE DERIVATIVES AND USE OF SAME

(71) Applicant: SANOFI, Paris (FR)

(72) Inventors: Zsolt Parkanyi, Budapest (HU); Edit Alattyani, Budapest (HU); Zoltan Bugir, Érd (HU); Marton Harsanyi, Dunakeszi (HU)

(73) Assignee: SANOFI, Paris (FR)

( * ) Notice: Subject to any disclaimer, the term of this patent is extended or adjusted under 35 U.S.C. 154(b) by 32 days.

(21) Appl. No.: 14/647,017

(22) PCT Filed: Nov. 22, 2012

(86) PCT No.: PCT/EP2012/073321
§ 371 (c)(1),
(2) Date: May 22, 2015

(87) PCT Pub. No.: WO2014/079497
PCT Pub. Date: May 30, 2014

(65) Prior Publication Data
US 2015/0291536 A1   Oct. 15, 2015

(51) Int. Cl.
*C07D 233/94* (2006.01)

(52) U.S. Cl.
CPC .................. *C07D 233/94* (2013.01)

(58) Field of Classification Search
CPC .................................................. C07D 233/94
See application file for complete search history.

(56) References Cited

U.S. PATENT DOCUMENTS

| | | | |
|---|---|---|---|
| 3,299,090 | A | 1/1967 | Hoff et al. |
| 4,031,232 | A | 6/1977 | Winkelmann et al. |
| 4,042,705 | A | 8/1977 | Winkelmann et al. |

FOREIGN PATENT DOCUMENTS

| | | | | |
|---|---|---|---|---|
| DE | 24 59 395 | A1 | 6/1976 | |
| GB | WO 2011151651 | A1 * | 12/2011 | ............ C07D 401/12 |
| KR | WO 2005040127 | A1 * | 5/2005 | ............ C07C 309/66 |

OTHER PUBLICATIONS

Torreele et al. "Fexinidazole—A New Oral Nitroimidazole Drug Candidate Entering Clinical Development for the Treatment of Sleeping Sickness" PLOS 2010, 4, 1-15.*

Samant et al. "Compounds containing 2-substituted imidazole ring for treatment against human African trypanosomiasis" Bioorg. Med. Chem. Lett. 2011, 21, 1015-1018.*

Ayra et al. "Nitroimidazoles: Part XV—1-Methyl-5-nitro-2-oxy(mercapto)imidazoles, 1-Methyl-5-nitroimidazole-2-methanol(carboxaldehyde & glyoxalic ester) Derivatives & 1-Substituted 2-Methyl-5 & 4-nitroimidazoles" Ind. J. Chem. 1982, 21B, 1078-1086.*

Bahia, M.T. et al. (Nov. 1, 2012). "Fexinidazole: A Potential New Drug Candidate for Chagas Disease," *PLOS Neglected Tropical Diseases* 6(11):e1870, nine pages.

Chinese Search Report mailed Apr. 28, 2016 for Chinese Patent Application No. 201280077219.0 filed on Nov. 22, 2012, six pages.

Intellectual Property Office of Singapore Search Report completed on Sep. 14, 2015 for Singapore Patent Application No. 11201504047T filed on Nov. 22, 2016, three pages.

Intellectual Property Office of Singapore Written Opinion mailed on Dec. 4, 2015 for Singapore Patent Application No. 11201504047T filed on Nov. 22, 2016, six pages.

Chandorkar, J.G. et al. (Oct. 2007). "Synthesis of Tinidazole by Condensation-Oxidation Sequence Using $MoO_3/SiO_2$ Bifunctional Catalyst," *Catalysis Communications* 8(10):1550-1555.

International Search Report mailed on Jul. 29, 2013, for PCT Application No. PCT/EP2012/073321, filed on Nov. 22, 2012, four pages.

Samant, B.S. et al. (Feb. 1, 2011; e-pub. Dec. 10, 2010). "Compounds Containing 2-Substituted Imidazole Ring for Treatment Against Human African Trypanosomiasis," *Bioorg. Med. Chem. Lett.* 21(3):1015-1018.

Turrens, J.F. et al. Nov. 1996). "Inhibition of Trypanosoma Cruzi and T. Brucei NADH Fumarate Reductase by Benznidazole and Anthelmintic Imidazole Derivatives," *Mol. Biochem. Parasitol.* 82(1):125-129.

Wyllie, S. et al. (Feb. 1, 2012). "The Anti-Trypanosome Drug Fexinidazole Shows Potential for Treating Visceral Leishmaniasis," *Sci. Transl. Med.* 4(119):119re1, Sixteen Total Pages.

\* cited by examiner

*Primary Examiner* — Michael Barker
*Assistant Examiner* — Amanda L Aguirre
(74) *Attorney, Agent, or Firm* — Morrison & Foerster LLP

(57) ABSTRACT

Fexinidazole is prepared according to a method which comprises the following steps: a) reacting 1-methyl-2-hydroxymethyl-5-nitro-imidazole with methanesulfonyl chloride in the presence of a suspension of powdered alkaline carbonate in an anhydrous organic solvent suitable for performing nucleophile substitution reactions; b) adding to the resulting reaction medium a solution of 4-methyl-mercapto-phenol in the same organic solvent as referred to in step a); c) separating fexinidazole from the reaction mixture as its hydrochloride salt and d) converting said hydrochloride salt into fexinidazole and optionally, purifying the latter.

9 Claims, No Drawings

METHOD FOR PREPARING PHENYLOXYMETHYL-NITRO-IMIDAZOLE DERIVATIVES AND USE OF SAME

CROSS-REFERENCE TO RELATED APPLICATIONS

This application is a National Phase application under 35 U.S.C. §371 of International Application No. PCT/EP2012/073321 filed Nov. 22, 2012, the disclosure of which is incorporated herein by reference in its entirety.

FIELD OF THE INVENTION

The invention refers to a method for preparing phenyloxymethyl-nitro-imidazole derivatives useful as active components of various medicaments, more specifically 1-methyl-2-(4-methlymercapto-phenyloxymethyl)-5-nitro-imidazole, also known as fexinidazole.

BACKGROUND OF THE INVENTION

Nitro-imidazole derivatives, especially molecules comprising a 1-methyl-5-nitro-imidazole entity are representatives of a class of active ingredients used today in the treatment of various tropical diseases like e.g. amoebiasis or parasitosis such as trichomoniasis. Fexinidazole, in particular, is a promising drug candidate for the treatment of kinetoplastid diseases such as visceral leishmaniasis, Chagas disease and human African trypanosomiasis (sleeping sickness).

Several methods have been proposed in the past for preparing such nitro-imidazole derivatives and include catalysed condensation reaction steps of selected starting materials followed, if ever required, by subsequent oxidation of intermediate compounds—see e.g. Catalyst Communications 8 (2007) 1550-1555. Alternatively, according to U.S. Pat. No. 4,042,705, substituted 1-methyl-5-nitro-imidazole molecules are subject to condensation with a phenol derivative to afford 1-methyl-2(phenyloxymethyl)-5-nitroimidazoles: 1-methyl-2-(4-methlymercapto-phenyloxymethyl)-5-nitro-imidazole (fexinidazole) is one of the various compounds which can be prepared following the technique disclosed therein.

Despite of previous efforts, manufacturing fexinidazole industrially while keeping yield as high as possible and purity grade as required by the pharmaceutical regulations has not been optimally achieved yet. It was observed in the meantime that the crucial reaction step which would require strict technical monitoring consists of synthetizing the intermediate nitro-imidazole derivative which is subsequently subject to condensation with 4-mercaptomethyl-phenol, i.e. 1-methyl-2-chloromethyl-5-nitro-imidazole as referred to in U.S. Pat. No. 4,042,705. This disclosure, however, remains silent concerning the preparation of the said intermediate 2-chloromethyl derivative or its equivalents (alkyl, aryl, etc.).

In some instances moreover, trials performed have shown that specific intermediate 2-chloro-alkyl or aryl-derivatives, although quite attractive in theory, proved poorly stable if not dangerous to handle. It was further observed that the condensation reactions are leading, as usual, to substantial amounts of secondary material (impurities) and eventually to a modest overall reaction yield hardly acceptable for the industry. Last but not least some reaction steps required different solvents and/or catalysts and could not therefore allow an easy integration of all the reaction steps.

The invention avoids all the technical drawbacks observed until now and provides the skilled technician with a method which affords fexinidazole with a high grade of purity and which is definitely simpler and easier to implement in a dedicated factory. The invention is defined in the attached claims.

SUMMARY OF THE INVENTION

The invention refers to a method for preparing 1-methyl-2-(4-methlymercapto-phenyloxymethyl)-5-nitro-imidazole (compound I) which comprises the following steps:
a) reacting 1-methyl-2-hydroxymethyl-5-nitro-imidazole with methanesulfonyl chloride in the presence of a suspension of powdered alkaline carbonate in an anhydrous organic solvent suitable for performing nucleophile substitution reactions, while monitoring the reaction conditions in such a way to afford less than 3% area percent of each of the secondary compounds of formula II and III;
b) adding to the resulting reaction medium a solution of 4-methylmercapto-phenol in the same organic solvent as referred to in step a) while monitoring the reaction conditions in such a way to avoid dimerization of compound I into compound of formula V;
c) separating compound I from the reaction mixture as its hydrochloride salt and
d) converting said hydrochloride salt into compound I and, optionally, purifying the latter.

This invention further refers to 1-methyl-2-(4-methlymercapto-phenyloxymethyl)-5-nitro-imidazole as obtained by means of the method described here above as well as to the use of same as a medicament useful, in particular, for treating various parasitic diseases, in particular visceral leishmaniasis, Chagas disease and human African trypanosomiasis.

This invention is substantially distinct from the prior art concerning several aspects, especially when keeping into consideration a multistep chemical process:
   one uses and keeps the same solvent over the whole process;
   one uses and keeps the same catalyst for the first two steps of the process;
   one does neither isolate nor purify the intermediate mesylated compound resulting from step a).

It has been moreover observed that the remaining amounts of secondary reaction products (compounds II, III and V) in the reaction medium do not impair the yield of each reaction step or the purity of the isolated products, i.e. fexinidazole hydrochloride and fexinidazole base.

A well-tuned monitoring of the various parameters which characterize the invention is leading to a particularly favourable overall yield of fexinidazole when compared to that afforded using prior known techniques.

Formulae I to V shall appear in a separate section of the specification.

DETAILED DESCRIPTION OF THE INVENTION

According to the invention step a) comprises first the preparation of a suspension of powdered alkaline carbonate in an anhydrous organic solvent suitable for nucleophile reactions: potassium carbonate is conveniently used therefore, preferably in the form of dry powder having an average particle size of <0.1 mm for min 95% of the whole amount under consideration. If not directly available as such form usual suppliers potassium carbonate is consequently ground on site until achievement of the predefined particle size.

The organic solvent referred to above is conveniently a polar aprotic organic solvent selected from aliphatic ketones, preferably a C3 to C5 aliphatic ketone such as e.g. acetone. Acetonitrile can also be used within the same context. According to the invention, the selected organic solvent is used for any of the reaction steps of the whole process, even including washing operations like e.g. washing of the crude and the purified fexinidazole crystals before final drying. Concerning acetone more specifically, one uses an anhydrous product as obtained from industrial suppliers and which exhibits e.g. a purity grade of at least 99.0%.

The addition of methanesulfonyl chloride solution to the suspension 1-methyl-2-hydroxymethyl-5-nitro-imidazole according to step a) initiates a strong exothermic reaction which requires careful monitoring of both the period of addition and the stabilization of the reaction temperature to a level optimally comprised between 10 and maximum 20° C. This type of control as well as that of the addition period is preferred for avoiding the formation of side products such as compounds II and III; in general said addition period varies usually from 90 to 150, preferably from 100 to 140 min. When step a) is carried out at a pilot plant scale (5 kg) this reaction step is leading to 2 to maximum 3 area percent of compound II, respectively to 1 to maximum 3 area percent of compound III.

According to the invention, the intermediate compound IV, i.e. 1-methyl-2-(methoxy-methylsulfonyl)-5-nitro-imidazole is not isolated from or, worded differently, is kept as is in the reaction medium of step a) and, similarly, the excess of unreacted 1-methyl-2-hydroxymethyl-5-nitro-imidazole is not withdrawn for said reaction medium either. The same applies to compounds II and III which, surprisingly, do not interfere negatively with the subsequent reaction steps.

According to the invention, step b) comprises the addition of 4-methylmercapto-phenol to the reaction medium resulting from step a) here above wherein said 4-methylmercapto-phenol reacts with the intermediate compound IV

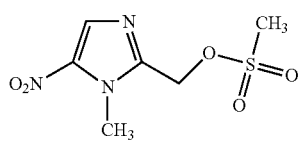

(IV)

which is present in the reaction medium of step a). The control of the reaction temperature is also preferred although this addition is not as exothermic as the previous one; addition of 4-methylmercaptophenol is usually performed at room temperature, preferably not exceeding 25 to 30° C. The completion of the reaction also requires additional heating: consequently, the temperature of the reaction medium is, preferably, progressively raised from 25 to max 50° C. as long as the expected yield of condensation product (fexinidazole) is not achieved. At the pilot plant scale addition and subsequent heating operations usually extend over 90 to maximum 150 min.

The adequate monitoring of the technical conditions of step b) avoids the formation of significant amounts of a fexinidazole dimer of formula V which is anyway detected in proportions definitely lower than 0.5 area percent even when step b) is carried out at a pilot plant scale.

Steps c) and d), eventually, can be carried out according to the usual practice and, whenever required, purification of the crude fexinidazole can be carried out as illustrated below.

In the examples disclosed here below the temperatures are provided as fixed values including a plus/minus 3° C. variation and the technical operations (mixing, adding, stirring, heating, cooling, etc.) are performed at fixed average temperatures in the various cases selected for illustrating in details the method of the invention. Variations in reaction time (operations) are nevertheless mentioned when material.

Unless specified differently all the operations are carried out under nitrogen atmosphere; room temperature means 20-25° C. The various chemicals used below are all obtained from usual industrial suppliers.

Unless specified differently all the % values provided here below about the purity of the various chemicals used are weight percent.

Example 1

1.1 (Step a)

Pouring at room temperature into a vessel fitted for performing under controlled atmosphere 250 g (315 ml) of anhydrous acetone (water content 0.1 mg/100 ml; purity according to GC analysis 100%), 78.50 g (0.5 m) of 1-methyl-2-hydroxymethyl-5-nitro-imidazole (purity 99.2%) and 233.50 g (1.7 m) of powdered potassium carbonate (assay 103%; 95%<0.1 mm) and stirring at room temperature until complete homogenization of the suspension. Then cooling down to 10° C., while still stirring and keeping the reaction medium as is for 60 min.

Preparing separately a solution of methanesulfonyl chloride in acetone (100% pure) by adding progressively 65.0 g (0.5 m) of methanesulfonyl chloride (purity >99.6%) to 100 g (125 ml) anhydrous acetone (water content 0.1 mg/100 ml; purity according to GC analysis 100%) permanently kept at 5° C.

Adding the acetone solution to the suspension referred to here above over a period of 90 min while keeping the reaction mixture at around 15° C. under stirring. Once the addition of the acetone solution is completed, the reaction mixture is further stirred at 15° C. for a maximum period of 15 min.

Eventually, heating progressively the reaction medium from 15 to 25° C. over a period of maximum 60 min and proceeding to the subsequent step.

1.2 (Step b)

Preparing a solution of 4-methylmercapto-phenol in acetone from 70.0 g (0.5 m) of 4-methylmercapto-phenol (purity >99.9%) and 70.0 g (90 ml) anhydrous acetone (100% pure), then adding the latter to the reaction medium of step a) over a period of 120 min while keeping the reaction mixture under constant stirring at 28° C.; stirring is performed thereafter at this temperature for 3 further hours. Heating progressively the resulting reaction medium from 28 to 50° C. over a period of 50 min; eventually keeping stirring for an additional period of maximum 60 min at 50° C. before pouring 500 ml of preheated water (68° C.) onto the above reaction mixture (quenching). Stirring the whole mass at 55° C. until complete dissolution of the components, then separating the aqueous lower phase from the acetone phase for elimination and eventually keeping the remaining acetone phase at 50° C. for the subsequent step.

1.3 (Step c)

100.0 g (1.0 m) of (36.7% volume) aqueous hydrochloric acid have been progressively added to the acetone solution of step b), i.e. over 60 min, under stirring and while still keeping the reaction mixture at 50° C. Cooling down the resulting mixture progressively from 50 to 15° C. to initiate crystallization of the hydrochloride salt and keeping the whole mass under stirring over an additional period of 60 min before filtration. Washing twice the crystallized hydrochloride salt with twice 160 ml acetone to afford 148 g of "wet" fexinidazole hydrochloride—yield ca. 72% (weight).

1.4 (Step d1: Obtention of Crude Fexinidazole Base)

Suspending the "wet" fexinidazole hydrochloride (148 g) resulting from step c) in 420 ml acetone (100% pure) and heating up to 52° C. the suspension before adding thereto 115 ml of preheated (52° C.) water.

Adding to the above mixture 66.0 g of 25% aqueous ammonia over a period of 60 min while keeping the reaction temperature at 52° C. and stirring it further on until complete dissolution. After keeping the whole reaction mixture for 20 min without stirring and separating the lower aqueous phase from the reaction medium, one adds 560 ml water to the remaining acetone phase to initiate fexinidazole base crystallization and eventually cool down the whole to 5° C. for 60 min.

After filtration and washing the solids with 200 ml of water one collects 120 g of "crude" fexinidazole—yield ca. 67.5% (weight) depending on remaining traces of acetone.

1.5 (Step d2: Isolation and Purification of Fexinidazole Base)

Suspending 120 g of crude fexinidazole base of step d1) in 235 ml of acetone (purity 100%), heating up to 58° C. until complete dissolution, adding 0.6 g of powdered charcoal to the heated solution and keeping stirring for 15 min before filtration. Washing the filter with hot (55-58° C.) acetone, then cooling the filtered solution down to 0° C. to afford fexinidazole crystals, filtering and washing the latter twice with 80 ml acetone (100% pure) and eventually drying on air at 40° C. to get 88.7 g of fexinidazole (purity grade see below)—yield 65% (weight).

Example 2 (Operational Variants)

2.1 Step a: the addition of methanesulfonyl chloride, which is strongly exothermic, can be performed over a period extending from 60 to 120 min provided cooling is sufficiently efficient for keeping the reaction temperature between min 10 and maximum 20° C.

2.2 Step b: the addition of the acetone solution of 4-methylmercapto-phenol can be performed over a period extending from 100 to 140 min while keeping an efficient stirring of the reaction mixture which density of same is progressively increasing.

Several batches have been conducted when applying technical conditions varying within the above ranges and still lead to similar overall yields of fexinidazole.

Example 3 (Analytics)

Each reaction step is monitored according the parameters initially selected and followed by means of HPLC analysis of dedicated samples taken from the relevant reaction medium, usually at the end of each addition step or just before full achievement of same.

There is provided below a sequence of HPLC analysis which applies to the processes referred to in Example 1; "%" refers here to area percent of each of the relevant peak analysed.

Step a: a sample is taken from the reaction mixture after complete addition of the methanesulfonyl chloride solution and subsequent stirring over 60 min and subjected to HPLC.

Column: Waters X Terra MS-C18 3.5 μm 3.0×100 mm—Temperature 30° C.—Mobile phase A: 0.1% formic acid in water—Mobile phase B: 0.1 formic acid in acetonitrile—Gradient elution program: min 0: 95 A/5 B; min 20: 0 A/100 B; min 22: 95 A/5 B; min 27: 95 A/5 B—Flow 0.5 ml/min—Injected volume 3 μl—Acquisition time 27 min—Detection wavelength 315 nm.

Results: 1-methy-2-hydroxymethyl-5-nitro-imidazole 8.5%; compound IV 85.2%; compound II 2.1%; compound III 1.08%.

Step b: a sample is taken from the reaction mixture immediately after complete addition of the 4-methylmercapto-phenol solution and subjected to HPLC.

The same analytical conditions as those defined above in step a) apply except the detection wavelengths: 315 and 254 nm.

Results: 1-methy-2-hydroxymethyl-5-nitro-imidazole 6.9%; compound IV 0.1%; compound II 1.6%; compound III 1.6%; 4-methylmercapto-phenol 16.4%; fexinidazole 73.6%.

At this stage one observes that a significant portion of untransformed 4-methylmercapto-phenol remains in the reaction mixture. Consequently, extension of reaction time and prolonged subsequent stirring allow to a significant decrease of the initial amount of 4-methylmercapto-phenol added to the mixture of step a.

Step c: The same analytical conditions as those defined above in step a) apply except the detection wavelengths: 315 and 254 nm.

Results: 1-methy-2-hydroxymethyl-5-nitro-imidazole 0.3%; compounds II, III and V less than 0.1%; fexinidazole hydrochloride 99.4%.

Step d1: The same analytical conditions as those defined above in step a) apply except the detection wavelengths: 315 and 254 nm.

Result: "crude" fexinidazole base 99.9%.

Step d2: The same analytical conditions as those defined above in step a) apply except the detection wavelengths: 315 and 254 nm. In addition thereto, the purity of fexinidazole is further confirmed by IR spectroscopy and by means of perchloric acid titration as well.

Results: fexinidazole 99.8%; water content 0.02%; sum of detectable impurities 0.003%; acetone 380 ppm.

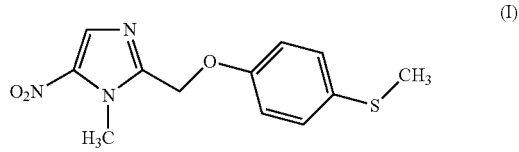 [SMILES: CSc1ccc(OCc2ncc([N+](=O)[O-])n2C)cc1]

(I)

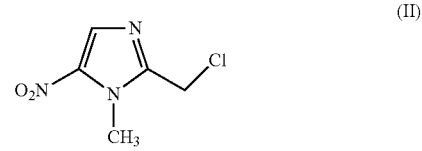

(II)

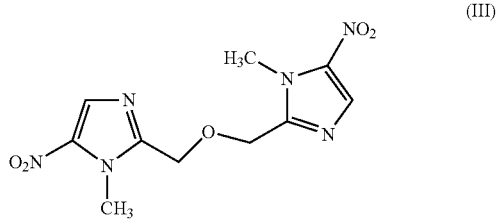

(III)

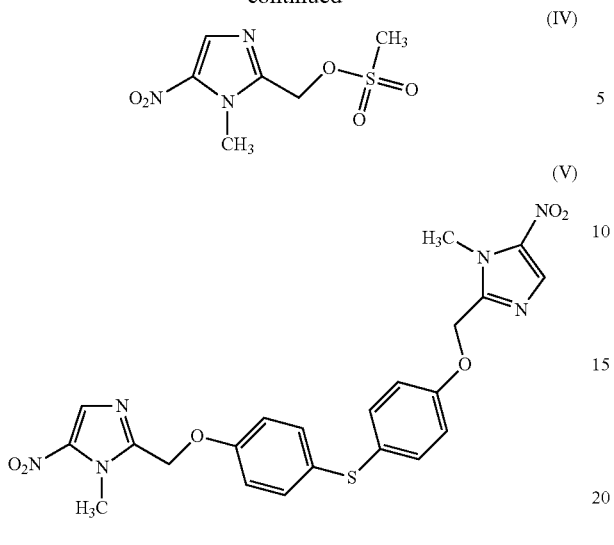

The invention claimed is:

1. A method for preparing 1-methyl-2-(4-methylmercapto-phenyloxymethyl)-5-nitro-imidazole having the formula

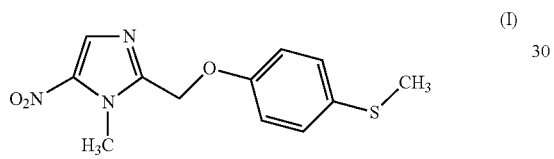

which comprises the steps of:
a) reacting 1-methyl-2-hydroxymethyl-5-nitro-imidazole with methanesulfonyl chloride in the presence of a suspension of powdered alkaline carbonate in an anhydrous organic solvent suitable for performing nucleophile substitution reactions while keeping the reaction medium at a temperature not exceeding 20° C. so as to afford less than 3 area percent, relative to the total area of the resulting reaction components of step a) detected by liquid chromatography, of each of the following secondary compounds of formula

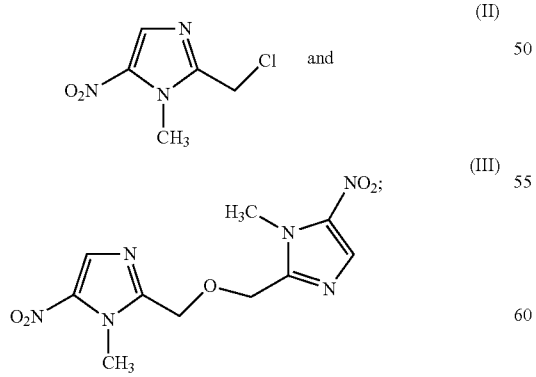

b) adding to the resulting reaction medium a solution of 4-methylmercapto-phenol in the anhydrous organic solvent used in step a) while keeping the reaction medium at a temperature not exceeding 30° C. so as to avoid dimerization of the compound of formula I into the compound of formula and heating thereafter the resulting reaction mixture up to 50° C.;

c) separating the compound of formula I from the reaction mixture as its hydrochloride salt; and d) converting said hydrochloride salt into the compound of formula I and, optionally, purifying the compound of formula I.

2. The method of claim 1, wherein the anhydrous organic solvent suitable for performing nucleophile substitution reactions is a polar aprotic organic solvent.

3. The method of claim 2, wherein the polar aprotic organic solvent is an aliphatic ketone.

4. The method of claim 1, wherein the powdered alkaline carbonate is potassium carbonate.

5. The method of claim 1, which comprises adding 4-methylmercapto-phenol, in the form of a solution in the same solvent used in step a), to the reaction mixture resulting from step a) while keeping the reaction medium at a temperature not exceeding 25° C., and heating thereafter the resulting reaction mixture up to 40° C.

6. The method of claim 1, which further comprises adding preheated water to the reaction mixture resulting from step b) prior to transforming the compound of formula I into its hydrochloride salt according to step c).

7. The method of claim 1, which comprises filtering off said hydrochloride salt from the reaction mixture resulting from step c), and in step d) subsequently subjecting said hydrochloride salt to alkalinisation by means of ammonia in an aqueous organic media.

8. The method of claim 2, wherein the polar aprotic organic solvent is a C3 to C5 aliphatic ketone.

9. The method of claim 2, wherein the polar aprotic organic solvent is acetone or acetonitrile.

* * * * *